(12) United States Patent
Heftman

(10) Patent No.: US 10,143,459 B2
(45) Date of Patent: Dec. 4, 2018

(54) INTERNAL RETRACTOR

(75) Inventor: Gilad Heftman, Kibutz Ein Gev (IL)

(73) Assignee: Virtual Ports Ltd., Caesarea (IL)

( * ) Notice: Subject to any disclaimer, the term of this patent is extended or adjusted under 35 U.S.C. 154(b) by 858 days.

(21) Appl. No.: 13/808,654

(22) PCT Filed: Jul. 5, 2011

(86) PCT No.: PCT/IL2011/000525
§ 371 (c)(1),
(2), (4) Date: May 28, 2013

(87) PCT Pub. No.: WO2012/004787
PCT Pub. Date: Jan. 12, 2012

(65) Prior Publication Data
US 2013/0237768 A1 Sep. 12, 2013

Related U.S. Application Data

(60) Provisional application No. 61/361,442, filed on Jul. 5, 2010, provisional application No. 61/422,661, filed on Dec. 14, 2010.

(51) Int. Cl.
| | |
|---|---|
| *A61B 1/32* | (2006.01) |
| *A61B 17/02* | (2006.01) |
| *A61B 17/00* | (2006.01) |
| *A61B 17/04* | (2006.01) |

(Continued)

(52) U.S. Cl.
CPC ........ *A61B 17/0218* (2013.01); *A61B 17/122* (2013.01); *A61B 2017/00876* (2013.01); *A61B 2017/00951* (2013.01); *A61B 2017/00991* (2013.01); *A61B 2017/0464* (2013.01); *A61B 2017/306* (2013.01)

(58) Field of Classification Search
CPC .............. A61B 17/0218; A61B 17/122; A61B 2017/00991
USPC ......................... 600/201, 203, 204, 227–235
See application file for complete search history.

(56) References Cited

U.S. PATENT DOCUMENTS 5,307,790 A * 5/1994 Byrne .................... A61B 17/02
                                                                24/20 R
5,582,577 A * 12/1996 Lund .................. A61B 17/0218
                                                                600/204
(Continued)

*Primary Examiner* — Si Ming Ku
(74) *Attorney, Agent, or Firm* — Dekel Patent Ltd.; David Klein

(57) ABSTRACT

The present invention provides a retraction device for retraction of an organ within the abdominal cavity, comprising: a. at least one first anchoring means reversibly attached to a first anchoring point within said abdominal cavity; b. at least one second anchoring means reversibly attached to a second anchoring point within said abdominal cavity; and, c. at least one supporting member, defining a predetermined geometrical structure, interconnecting said first anchoring means and said second anchoring means, at least partially support said organ; wherein said at least one supporting member is characterized by a substantially rigid structure, such that said at least one supporting member is substantially not deformed in any direction outside the plane defining said supporting member when a mechanical force is applied, by said organ, on said rigid structure of said supporting member when said organ is retracted via said retraction device.

9 Claims, 20 Drawing Sheets

(51) Int. Cl.
    *A61B 17/122*     (2006.01)
    *A61B 17/30*      (2006.01)

(56) References Cited

U.S. PATENT DOCUMENTS

| | | | |
|---|---|---|---|
| 2006/0276871 A1* | 12/2006 | Lamson | A61F 2/82 623/1.11 |
| 2007/0156023 A1* | 7/2007 | Frasier | A61B 17/0293 600/206 |
| 2007/0239161 A1* | 10/2007 | Giger | A61B 17/8076 606/86 A |
| 2009/0030284 A1* | 1/2009 | Cole | A61B 1/00078 600/206 |
| 2009/0043246 A1* | 2/2009 | Dominguez | A61B 17/0218 604/21 |
| 2009/0198107 A1* | 8/2009 | Park | A61B 17/02 600/215 |
| 2010/0298629 A1* | 11/2010 | Huang | A61B 17/0218 600/37 |
| 2011/0087067 A1* | 4/2011 | Rodrigues, Jr. | A61B 17/0218 600/37 |

\* cited by examiner

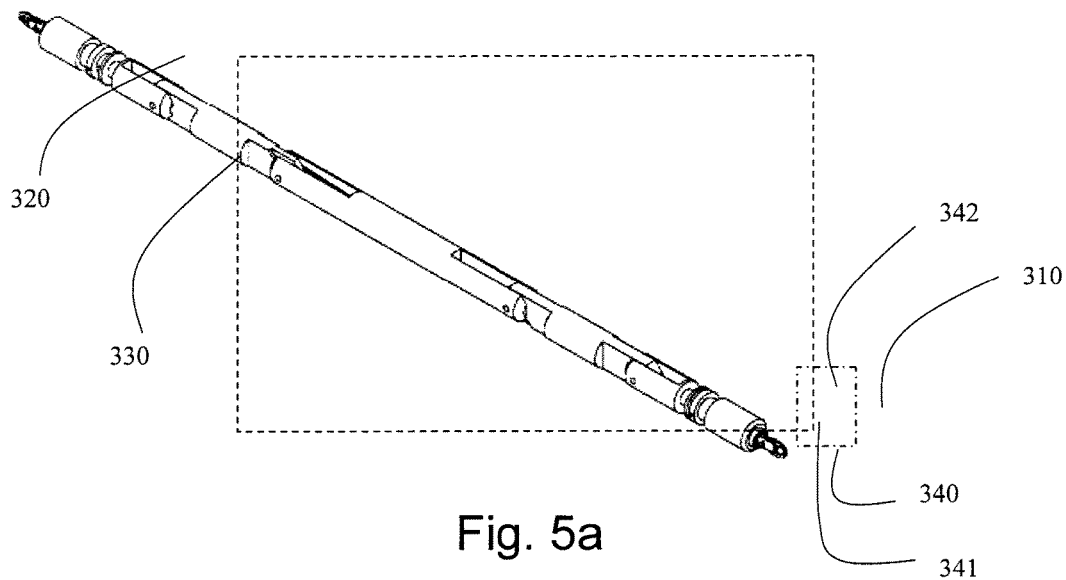
Fig. 5a
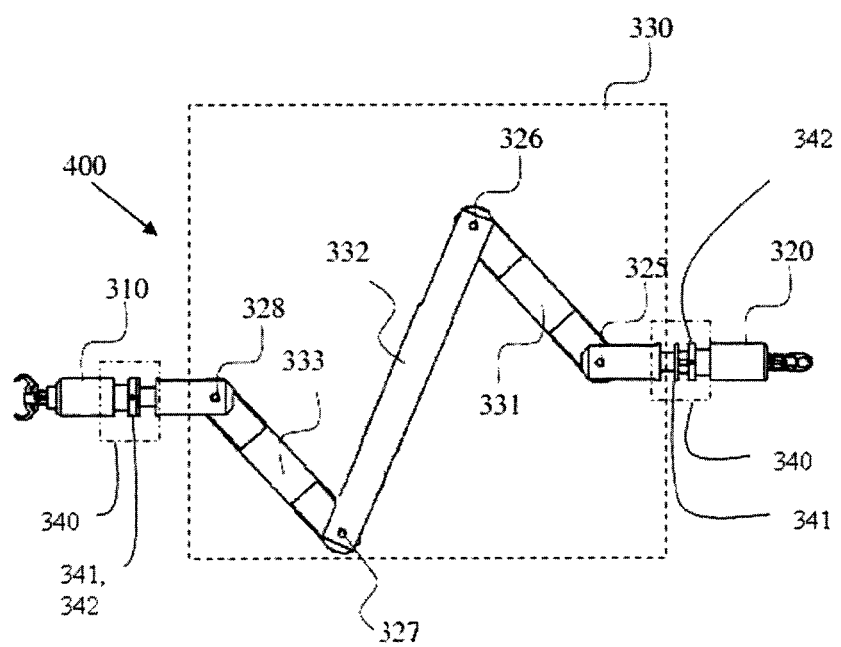
Fig. 5b

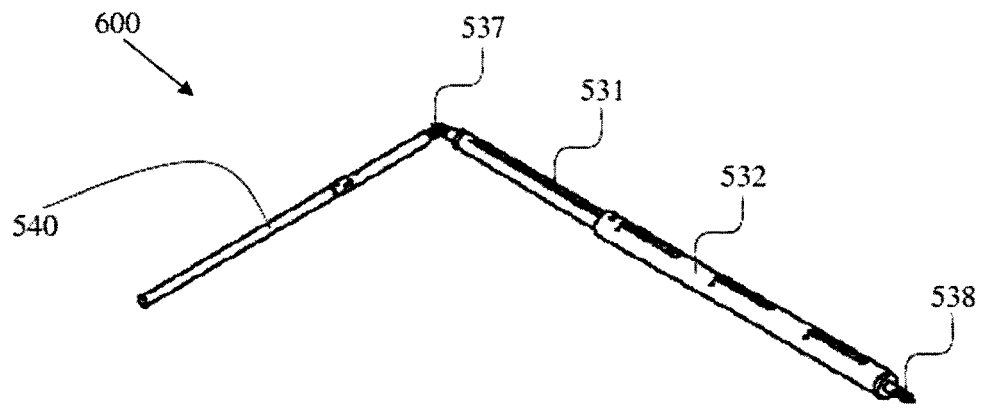
Fig. 7a₁
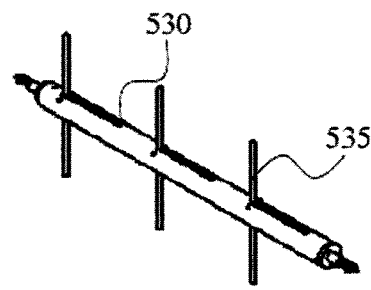
Fig. 7a₂
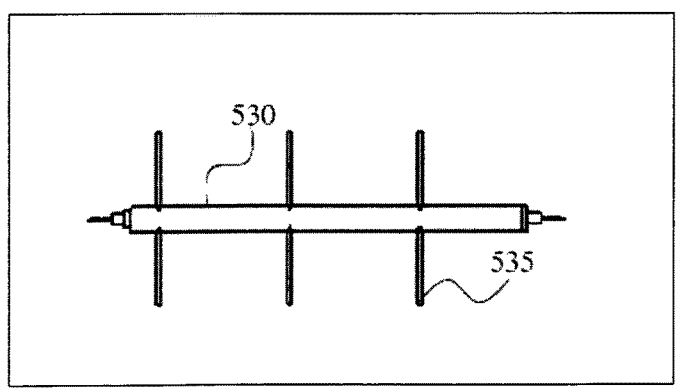
Fig. 7a₃

INTERNAL RETRACTOR

CROSS REFERENCE TO RELATED APPLICATIONS

This application is a national phase of International Application No. PCT/IL2011/000525, filed 5 Jul. 2011, now expired, which claims priority from U.S. Provisional Application No. 61/361,442, filed 5 Jul. 2010, and U.S. Provisional Application No. 61/422,661, filed 14 Dec. 2010, all of which are hereby incorporated by reference in their entireties.

FIELD OF THE INVENTION

The present invention generally relates to a surgical device, and more specifically, to a retraction device for lifting and supporting various organs within the abdominal cavity.

BACKGROUND OF THE INVENTION

During surgical procedures, there may be a requirement for the retraction of organs, so the field of view or work area will be clear. For example, a segment or lobe of the liver may need to be held back in order to perform surgery on a segment of the stomach. This process can be demanding and typically can require an extra person to hold a conventional retractor. This procedure is even more challenging during minimally invasive surgery (MIS) where port and surgical technician may be devoted primarily to holding tissue back from the field of view or work area.

US patent application US2009/0198107 (referred hereinafter as '107) discloses a device for use during surgical or non-surgical procedures, which can move items from the field of view or work space. Retraction of items during any surgical or non-surgical procedure moves the items from the field of view or work space. The flexibility and compactness of a retraction device can make it suitable for surgery, especially minimally invasive surgery (MIS).

The main distinction between the retraction device disclosed in '107 and the retraction device of the present application is the fact that the '107 device is made of non-rigid structure which deform under application of forces. For example, the device of patent application '107 will bent (under force), and thereby increase the tension forces which are applied on the abdominal wall. Such tension forces may harm the tissues involved and cause irreversible damage. Furthermore, such bending decreases the amount of organ retraction provided.

Thus, there is a long felt need to provide a retraction device which minimized the tension forces applied on the abdominal wall.

SUMMARY OF THE INVENTION

It is one object of the present invention to provide a retraction device useful in laparoscopic surgery and especially in minimally invasive surgeries for retraction of an organ within the abdominal cavity of the human body. The retraction device comprises:
 a. at least one first anchoring means adapted to be reversibly attached to a first anchoring point within said abdominal cavity.
 b. at least one second anchoring means adapted to be reversibly attached to a second anchoring point within said abdominal cavity.
 c. at least one supporting member, defining a predetermined geometrical structure, interconnecting the first anchoring means and the second anchoring means, adapted to at least partially support the organ, such that the organ is retracted.

It is within the scope of the present invention to provide the retraction device as defined above, wherein said at least one supporting member is characterized by a substantially rigid structure, such that the at least one supporting member is substantially not deformed when mechanical force, cause by said organ, is applied on the geometrical structure of the supporting member when the organ is retracted via the retraction device.

It is another object of the present invention to provide the retraction device as defined above, wherein said mechanical force applied by said organ is perpendicular to said supporting member.

It is another object of the present invention to provide the retraction device as defined above, wherein said supporting member is defined by a plane; further wherein said perpendicular force applied on said supporting member does not result in any development of tangential force in said plane.

It is another object of the present invention to provide the retraction device as defined above, wherein said supporting member is defined by a plane; further wherein said perpendicular force applied on said supporting member does not result in any change in tangential force in said plane.

It is another object of the present invention to provide the retraction device as defined above, wherein said mechanical force applied by said organ is positioned at an angle of about 0 to about 90 relatively to said supporting member's plane's normal.

It is another object of the present invention to provide the retraction device as defined above, wherein the mechanical force is applied on the geometrical structure substantially perpendicularly.

It is another object of the present invention to provide the retraction device as defined above, wherein said supporting member is characterized by at least one selected from a group consisting of (a) predetermined size; (b) predetermined length; (c) predetermined cross section; (d) predetermined shape; or any combination thereof; such that, when a perpendicular force is applied on said supporting member, said at least one selected from a group consisting of (a) predetermined size; (b) predetermined length; (c) predetermined cross section; (d) predetermined shape is substantially not deformed.

It is another object of the present invention to provide the retraction device as defined above, wherein said supporting member is defined by a plane; such that when a perpendicular force to said plane, is applied on said supporting member; said supporting member is substantially not deformed in any plane outside said plane.

It is another object of the present invention to provide the retraction device as defined above, wherein said supporting member is defined by a plane; such that when a perpendicular force, to said plane, is applied on said supporting member; said supporting member is substantially not deformed in a perpendicular direction to said plane.

It is another object of the present invention to provide the retraction device as defined above, wherein the structural properties of said rigid structure is characterized by at least one mechanical property selected from a group consisting of: non-bendable, a non-flexible structure, a non-twistable structure, a non-elastic structure, or any combination thereof due to perpendicular force applied on said supporting member.

It is another object of the present invention to provide the retraction device as defined above, wherein the rigidity of the supporting member is adapted to reduce the tension forces actuated by the first anchoring means and the second anchoring means on the first and second anchoring points, relatively to a non-rigid supporting member.

It is another object of the present invention to provide the retraction device as defined above, wherein when a retraction force F is applied by the organ on the at least one supporting member, the tension forces actuated on each of the first and second anchoring points is about 0.5° F.

It is another object of the present invention to provide the retraction device as defined above, wherein when a tangential force is applied on said at least one supporting member, the shape of said at least one supporting member is changed.

It is another object of the present invention to provide the retraction device as defined above, wherein the geometrical structure is characterized by dimensions selected from: 1D, 2D, 3D, or any combination thereof.

It is another object of the present invention to provide the retraction device as defined above, wherein the geometrical structure is selected from a group consisting of: an array of interconnected wires, a surface, a plane, a platform, or any combination thereof.

It is another object of the present invention to provide the retraction device as defined above, wherein the supporting member is deployable within the abdominal cavity and is characterized by at least two configurations: (i) a FOLDED CONFIGURATION; and, (ii) a DEPLOYED CONFIGURATION;

It is another object of the present invention to provide the retraction device as defined above, wherein said supporting member is characterized by a default configuration which is selected from said FOLDED CONFIGURATION and said DEPLOYED CONFIGURATION.

It is another object of the present invention to provide the retraction device as defined above, wherein in the FOLDED CONFIGURATION, the geometrical structure has dimensions of 1D, and in the DEPLOYED CONFIGURATION the geometrical structure of has dimensions selected from a group consisting of: 1D, 2D, 3D, or any combination thereof.

It is another object of the present invention to provide the retraction device as defined above, wherein each of the at least one first anchoring means and the at least one second anchoring means is selected from the group consisting of: vacuum means, magnetic means; mechanical means, adhesive means or any combination thereof.

It is another object of the present invention to provide the retraction device as defined above, wherein said supporting member comprises at least two hinged elements adapted to provide the deployment of said retraction device.

It is another object of the present invention to provide the retraction device as defined above, wherein each of the at least one first anchoring means and the at least one second anchoring means comprises a plurality of attachment means selected from the group consisting of: clips, clamps, fasteners, binding means, connecting means, vacuum cups, magnetic means, mechanical means, adhesive means, needle, spike, peg, hook, or any combination thereof.

It is another object of the present invention to provide the retraction device as defined above, further comprising controlling means releasably attached to the retraction device, adapted to (i) introduce the retraction device into the abdominal cavity; (ii) to extract the retraction device from the abdominal cavity; and, (iii) to relocate the retraction device within the abdominal cavity; the controlling means being at least partially operated by from outside the body.

It is another object of the present invention to provide the retraction device as defined above, wherein the retraction device is adapted to relocate the organ from one predetermined location to another predetermined location within the abdominal cavity of the human body.

It is another object of the present invention to provide the retraction device as defined above, wherein said supporting member comprises an intermediate member adapted to couple said supporting member to at least one selected from a group consisting of said first anchoring means, said one second anchoring means or any combination thereof.

It is another object of the present invention to provide a method for internally retracting an organ within abdominal cavity of the human body during minimally invasive surgeries, the method comprising steps of:
a. Obtaining a retraction device useful in minimally invasive surgeries for retraction of an organ within the abdominal cavity of the human body, the retraction device comprising: (i) at least one first anchoring means adapted to be reversibly attached to a first anchoring point within said abdominal cavity; (ii) at least one second anchoring means adapted to be reversibly attached to a second anchoring point within said abdominal cavity; and, (iii) supporting member, defining a predetermined geometrical structure, interconnecting the first anchoring means and the second anchoring means.
b. Inserting the retraction device into the abdominal cavity by means of an introducer.
c. Reversibly attaching the at least one first anchoring means to the first anchoring point.
d. Reversibly attaching the at least one second anchoring means to the second anchoring point while retracting the organ.
e. Supporting the organ by the supporting member, and thereby retracting the organ.

It is within the scope of the present invention that the method as defined above, further comprises step of providing the at least one supporting member, wherein the at least one supporting member is characterized by a substantially rigid structure, thereby substantially preventing deformation of the at least one supporting member when mechanical force is applied on the geometrical structure of the supporting member when the organ is retracted via the retraction device.

It is another object of the present invention to provide the retraction method as defined above, wherein said mechanical force applied by said organ is perpendicular to said supporting member.

It is another object of the present invention to provide the retraction method as defined above, wherein said supporting member is defined by a plane; further wherein said perpendicular force applied on said supporting member does not result in any development of tangential force in said plane.

It is another object of the present invention to provide the retraction method as defined above, wherein said supporting member is defined by a plane; further wherein said perpendicular force applied on said supporting member does not result in any change in tangential force in said plane.

It is another object of the present invention to provide the retraction method as defined above, wherein said mechanical force applied by said organ is positioned at an angle of about 0 to about 90 relatively to said supporting member's plane's normal.

It is another object of the present invention to provide the retraction method as defined above, wherein said supporting member is characterized by at least one selected from a group consisting of (a) predetermined size; (b) predetermined length; (c) predetermined cross section; (d) predetermined shape; or any combination thereof; such that, when a perpendicular force is applied on said supporting member, said at least one selected from a group consisting of (a) predetermined size; (b) predetermined length; (c) predetermined cross section; (d) predetermined shape is substantially not deformed.

It is another object of the present invention to provide the retraction method as defined above, wherein said supporting member is defined by a plane; such that, when a perpendicular force to said plane, is applied on said supporting member; said supporting member is substantially not deformed in any plane outside said plane.

It is another object of the present invention to provide the retraction method as defined above, wherein said supporting member is defined by a plane; such that when a perpendicular force, to said plane, is applied on said supporting member; said supporting member is substantially not deformed in a perpendicular direction to said plane.

It is another object of the present invention to provide the retraction method as defined above, which further comprises step of applying mechanical force on the geometrical structure substantially perpendicularly.

It is another object of the present invention to provide the retraction method as defined above, which further comprises step of selecting a mechanical property of the rigid material from a group consisting of: non-bendable, non-flexible, non-twistable, non-elastic, or any combination thereof.

It is another object of the present invention to provide the retraction method as defined above, which further comprises step of applying a retraction force F by the organ on the supporting member, and thereby actuating tension forces on each of the first and second anchoring points of about 0.5*F.

It is another object of the present invention to provide the retraction method as defined above, further comprising step of applying a tangential force is on said at least one supporting member, thereby changing the shape of said at least one supporting member.

It is another object of the present invention to provide the retraction method as defined above, which further comprises step of selecting a geometrical structure of the supporting member with dimensions selected from a group consisting of: 2D, 3D, or any combination thereof.

It is another object of the present invention to provide the retraction method as defined above, which further comprises step of selecting the supporting member from a group consisting of: an array of interconnected wires, a surface, a plane, a platform, or any combination thereof.

It is another object of the present invention to provide the retraction method as defined above, which further comprises step of deploying the supporting member within the abdominal cavity; the supporting member characterized by at least two configurations: (i) a FOLDED CONFIGURATION; and, (ii) a DEPLOYED CONFIGURATION.

It is another object of the present invention to provide the retraction method as defined above, wherein in the FOLDED CONFIGURATION, the supporting member is characterized by a 1D geometrical structure, and in the DEPLOYED CONFIGURATION the supporting member is characterized by a geometrical structure of dimensions selected from: 2D, 3D, or any combination thereof.

It is another object of the present invention to provide the retraction method as defined above, further comprising step of providing said supporting member in a default configuration selected from said FOLDED CONFIGURATION and said DEPLOYED CONFIGURATION.

It is another object of the present invention to provide the retraction device as defined above, wherein each of the at least one first anchoring means and the at least one second anchoring means is selected from the group consisting of: vacuum means, magnetic means; mechanical means, adhesive means or any combination thereof.

It is another object of the present invention to provide the retraction method as defined above, which further comprises step of selecting each of the at least one first anchoring means and the at least one second anchoring means from the group consisting of: vacuum means, magnetic means; mechanical means, adhesive means or any combination thereof.

It is another object of the present invention to provide the retraction method as defined above, which further comprises steps of: providing the at least one first anchoring means and the at least one second anchoring means with a plurality of attachment means; and, selecting the attachment means from the group consisting of: clips, clamps, fasteners, binding means, connecting means, vacuum cups, magnetic means, mechanical means, needle, spike, peg, adhesive means or any combination thereof.

It is another object of the present invention to provide the retraction method as defined above, which further comprises steps of: releasable attaching a controlling means to the retraction device; introducing the retraction device into the abdominal cavity; extracting the retraction device from the abdominal cavity; and, relocating the retraction device within the abdominal cavity; the controlling means being at least partially operated by from outside the body.

It is another object of the present invention to provide the retraction method as defined above, which further comprises step of relocating the retraction device from one predetermined location to another predetermined location within the abdominal cavity of the human body.

It is another object of the present invention to provide the retraction method as defined above, wherein said supporting member comprises an intermediate member adapted to couple said supporting member to at least one selected from a group consisting of said first anchoring means, said one second anchoring means or any combination thereof.

BRIEF DESCRIPTION OF THE FIGURES

For a better understanding of the invention and to show how the same may be carried into effect, reference will now be made, purely by way of example, to the accompanying drawings in which like numerals designate corresponding elements or sections throughout.

With specific reference now to the drawings in detail, it is forced that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 5a-5b are specific embodiments of the retraction device of the present invention in its DEPLOYED and folded CONFIGURATION.

FIG. 7a1-7a3 is a specific embodiment of a telescopic retraction device of the present invention having side rods 535.

FIGS. 10b, 11b, 12b, 13b and 14b are schematic illustrations of FIGS. 10a, 11a, 12a, 13a and 14a.

Figure 1:
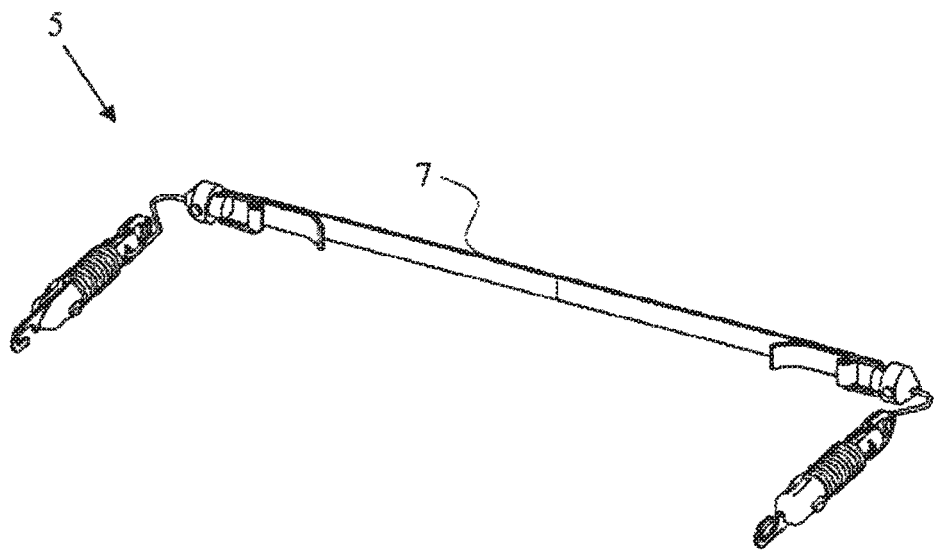
FIG. 1 is a schematic illustration of retraction device of the prior art.

The drawings together with the description make apparent to those skilled in the art how the invention may be embodied in practice.

DETAILED DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The device of the present invention provides a retraction device useful in minimally invasive surgeries for retraction of an organ within the abdominal cavity, said retraction device comprising:
a. at least one first anchoring means adapted to be reversibly attached to a first anchoring point within the abdominal cavity;
b. at least one second anchoring means adapted to be reversibly attached to a second anchoring point within the abdominal cavity; and,
c. at least one supporting member, defining a predetermined geometrical structure, interconnecting said first anchoring means and said second anchoring means, adapted to at least partially support said organ, such that said organ is retracted;

The at least one supporting member is characterized by a substantially rigid structure, such that said at least one supporting member is substantially not deformed outside the plane defining said supporting member, when a mechanical force is applied by the organ on the rigid structure of the supporting member when the organ is retracted via the retraction device.

According to one embodiment said retraction device can be non-invasively and removably attached to the undersurface of a patient's cavity, or to various tissues within a cavity.

The device is initially introduced through an opening in the cavity wall and then attached to some location on the undersurface of the cavity wall, by attachment means.

The term '1D' refers hereinafter to a one dimensional geometrical structure which is may be characterized by one coordinate adapted to specify each point on it. For example, a wire, a cord, a rod, a rope, etc. are 1D geometrical structures.

The term '2D' refers hereinafter to a two dimensional geometrical structure which requires two coordinated in order to specify each point of it.

The term 'leaf spring' refers hereinafter to a flat elastic element which can be made of any material with a polygonal or rounded cross sectional shape. The flat element is characterized by an ability to be bent in a desired direction when a predetermined force in a predetermined direction is applied on it.

The term 'rigid structure' refers hereinafter to a structure being characterized by at least one of the following:
(a) illustrating no deformation in the plane confining said rigid structure (in terms of size, shape, length, cross section or any combination thereof) to a normal force applied on the same; In other words, when normal forces are applied, no deformation in e.g., length is illustrated (again, in the plane confining said rigid structure); and hence, no tangential (i.e., parallel) forces will be created.
(b) When perpendicular forces are applied on said rigid structure, no development (or change) of tangential force to the plane confining said rigid structure are illustrated.
(c) having a degree of freedom of rotation or/and translation in the plane parallel (or enclosing) to said structure, but no degree of freedom in the two other planes perpendicular to said structure. In other words, the structure may illustrate deformation in the plane parallel to the same, but there will be no deformation to the plane perpendicular to the same.

The above definition of rigid is provided under the assumption that the friction between the rigid structure and the retracted organ (i.e., the element which eventually applies the vertical forces) is neglectable. In other words, the present invention defines the force applied on the rigid structure as a normal (i.e., vertical) force assuming there is no friction.

The term 'anchoring point' refers hereinafter to any physiological location within said abdominalcavity to which the device of the present invention may be attached to. For example, the anchoring point may be located on the internal abdominal wall, or an organ within said abdominal cavity. The anchoring point is located on the internal surface of said abdominal wall, such that creation of an opening at the location of the anchoring point for the retraction is prevented.

The term 'tangential' refers hereinafter to a direction of a tangent to the supporting member of the device.

According to another embodiment of the present invention, the term 'leaf spring' refers hereinafter to a flat rod which can be made of any material with polygonal or rounded cross section shape; furthermore, the rod's cross sections properties are chosen such that its height is smaller than its width so when axial force is applied; the buckling of the rod is in predetermined direction.

FIG. 1 illustrates the retraction device of the prior art, in which a retraction device 5 which comprises a non-rigid supporting member 7 (e.g., a plastic mesh, a silicon strip, etc.), which is deformable when a mechanical force is applied. As a result of this deformation, a high tension is applied on the abdominal wall. This high tension may cause damage to the tissue of the abdominal wall or may cause the retraction device to disconnect from the tissue.

Furthermore, the bending obtained substantially decreases the amount of organ retraction obtained.

As will be disclosed below, the present invention is intended to reduce this high tension applied of the abdominal wall, so as to prevent (or reduce) the damage to the tissue and prevent disconnection of the retraction device from the tissue, and to have farther retraction.

An additional advantage of the present invention over the prior art is the ability of the retraction device to be deployed. As will be disclosed below, in its DEPLOYED CONFIGURATION, the supporting member of the present invention is adapted to provide a surface which is adapted to support the organ. This surface is characterized by a 2D/3D wide area which improves the ability to support the organ, and differently from a 1D member with narrow area.

Figure 2:
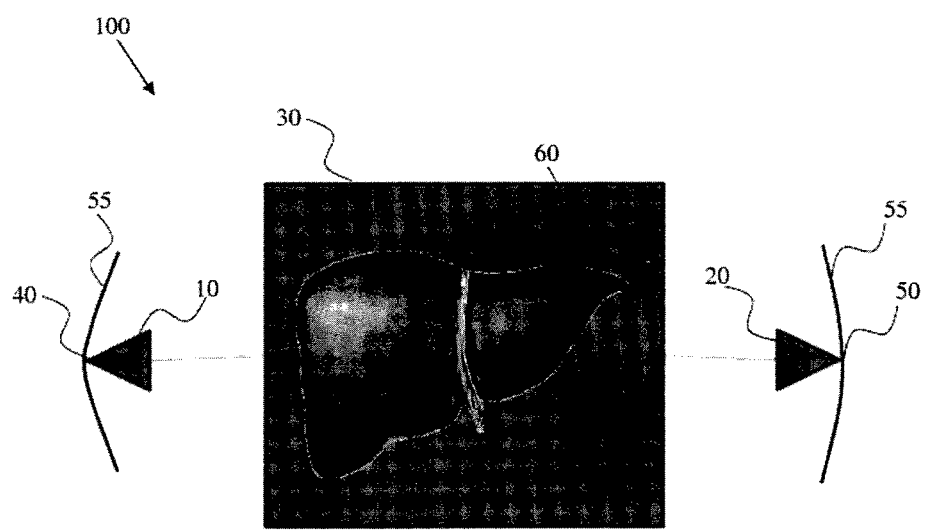
FIG. 2 is a schematic illustration of retraction device of the present invention.

Reference is now made to FIG. 2, which illustrates a specific embodiment of retraction device 100.

Retraction device 100 is useful in minimally invasive surgeries for retraction of an organ 60 within the abdominal cavity of the human body. By the retraction of organ 60, retraction device 100 is adapted to relocate organ 60 from one predetermined location to another predetermined location within the abdominal cavity of the human body.

According to this figure, retraction device 100 comprises the following components:
a. A first anchoring means 10 adapted to be reversibly attached to a first anchoring point 40 (e.g., on the internal abdominal wall 55);
b. A second anchoring means 20 adapted to be reversibly attached to a second anchoring point 50 (e.g., on the internal abdominal wall 55); and,
c. Supporting member 30, defining a predetermined geometrical structure, interconnecting the first anchoring means 10 and second anchoring means 20. Supporting member 30 adapted to at least partially support organ 60, such that organ 60 is retracted.

The supporting member 30 is characterized by a substantially rigid structure, such that supporting member 30 is substantially not deformed (e.g., not bent, not twisted, etc.) when a mechanical force is applied on the rigid structure of supporting member 30 (e.g., when organ 60 is placed on the supporting member 30). According to different embodiments of the present invention, first and second anchoring points 40 and 50 can be any physiological locations on the internal abdominal wall 55 to which first and second anchoring means 10 and 20 may be attached to.

The first and the second anchoring points 40 and 50 are located on the internal surface of the abdominal wall. According to this, an advantage provided by the device of the present invention is that the location of the anchoring point at an internal surface of the abdominal wall within the abdominal cavity prevents the creation of an additional opening in the patient's body. This avoidance of creating an additional opening in the patient's body is highly important in the field of laparoscopic surgeries. Each incision in the body of the patient, leaves scars, and requires recovery. Moreover, in creation of an additional incision, there is always a risk of infections. Therefore, creation of an additional incision in the body of the patient should be prevented if it possible.

By using the various attachment means provided by the device of the present invention, for the attachment of the first and the second anchoring means to the abdominal wall, the surgeon is able the change the direction of the retraction and the location of the anchoring point without creating additional openings at the abdominal wall.

According to some embodiments of the present invention, supporting member 30 may be characterized by a 1D, a 2D or a 3D geometrical structure.

According to various embodiments, this rigid structure of supporting member 30 may form one of the following structures: a plurality of rods, an array of interconnected rods (or wires), a telescopic structure, a surface, a plane, a platform, etc.

According to some embodiments of the present invention, the first anchoring means 10 and second anchoring means 20 may be selected from the group consisting of: vacuum means, magnetic means; mechanical means, adhesive means, etc.

According to other embodiments of the present invention, first anchoring means 10 and second anchoring means 20 may comprise a plurality of attachment means selected from the group consisting of: clips, clamps, fasteners, binding means, connecting means, vacuum cups, magnetic means, mechanical means, adhesive means, needle, hook, spike, peg, etc.

The main problem with the bendable retraction device of patent application '107, which the present invention is intended to solve, is an existence of high tension forces applied on the internal abdominal wall 55 (namely on the first/second anchoring point 40/50) when the device is used for the retraction of the organ. A further non neglectable issue is the bending of the '107 device. Such bending, as mentioned above, will decrease the amount of organ retraction eventually obtained.

These high tension forces are much lower in the device of the present invention, due to the design characteristics of retraction device 100, and more specifically, the rigidity of supporting member 30.

As will be seen in the following equations, $T>T_1$, for each $0°\leq\alpha\leq90°$.

Figure 3A:
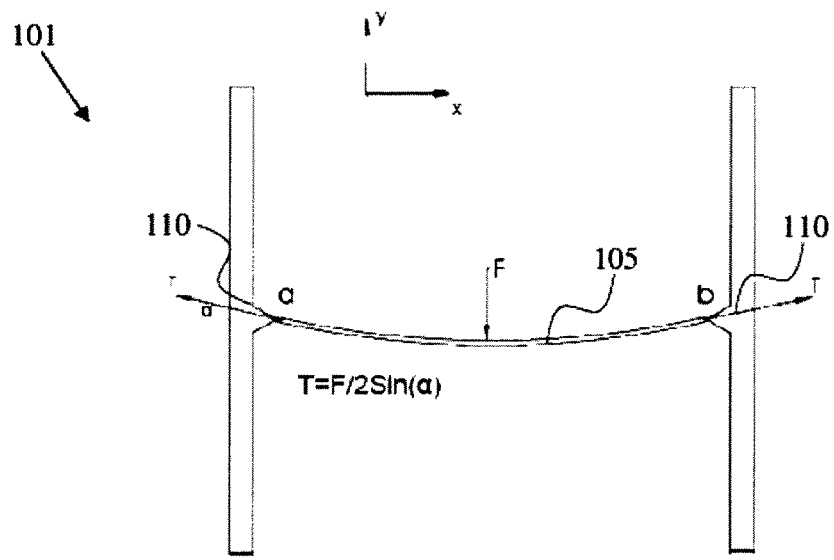
FIG. 3a-3b is an illustration of physical concepts and the advantages of the retraction device of the present invention over the prior art.
Figure 3B:
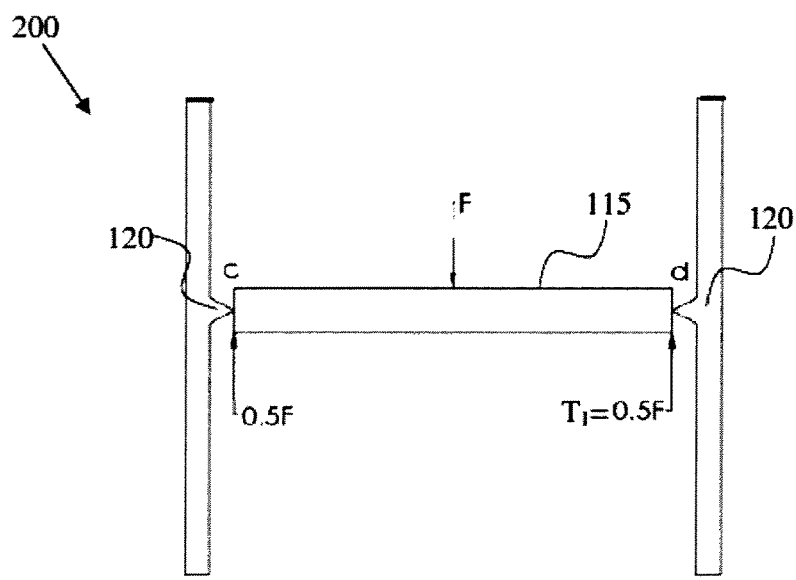

By referring to FIG. 2 and to FIGS. 3*a-b*, it can be easily concluded that the rigidity of supporting member 30 is adapted to reduce the tension force $T_1$ (in FIG. 3*b*) actuated by first anchoring means 10 and second anchoring means 20 on first and second anchoring points 40 and 50, relatively to a non-rigid supporting member and its tension force T (in FIG. 3*a*).

FIG. 3*a* illustrates a bendable retraction device 101 e.g., the device disclosed in US patent application '107. In this figure, a non-rigid (e.g., soft) supporting member 105 is attached to the internal abdominal wall 110 at two anchoring points a and b.

According to calculation performed by the inventors of the present invention, when a perpendicular force F is applied (e.g., by a retracted organ) on the non-rigid supporting member 105, the tension which is applied on the internal abdominal wall 110 is $T=F/(2*\sin(\alpha))$.

For example, when $\alpha=30°$, $T=F$.

FIG. 3*b* illustrates the rigid retraction device 200 of the present invention. In this figure, a rigid supporting member 115 is attached to the internal abdominal wall 120 at two anchoring points c and d. According to calculation performed by the inventors of the present invention, when force F is applied by a retracted organ on midpoint of rigid supporting member 115, the tension which is applied on the internal abdominal wall 120 is $T_1=F/2$.

According to the calculations presented above, the tension on the abdominal wall is reduced, when a rigid supporting member is used. Therefore, the damage which is/may be caused to the tissue of the abdominal wall is reduced/eliminated. Furthermore, the possibility of the retraction device to disconnect from the tissue is reduced.

It should be pointed out that, rigid supporting member as used above, is defined by at least one of the following:

(a) illustrating no deformation in the plane confining said rigid structure (in terms of size, shape, length, cross section or any combination thereof) to a normal force applied on the same; In other words, when perpendicular forces are applied, no deformation in e.g., length is illustrated (again, in the plane confining said rigid structure); and hence, no tangential (i.e., parallel) forces will be created.

(b) When perpendicular forces are applied on said rigid structure, no development (or change) of tangential force to the plane confining said rigid structure are illustrated.

(c) having a degree of freedom of rotation or/and translation in the plane parallel (or enclosing) to said structure, but no degree of freedom in the two other planes perpendicular to said structure. In other words, the structure may illustrate deformation in the plane parallel to the same, but there will be no deformation to the plane perpendicular to the same.

The above definition of rigid is provided under the assumption that the friction between the rigid structure and the retracted organ (i.e., the element which eventually applies the vertical forces) is neglectable. In other words, the present invention defines the force applied on the rigid structure as a normal (i.e., vertical) force assuming there is no friction.

Figure 4A:
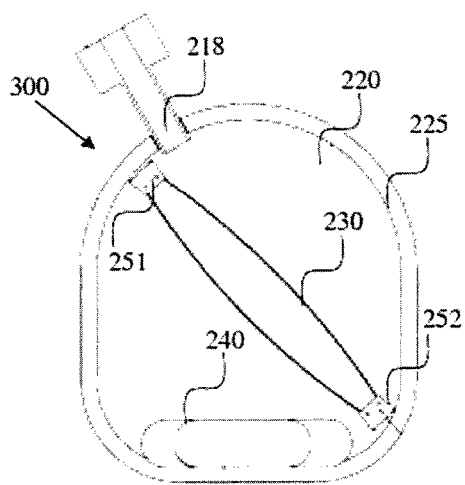
FIGS. 4a-4b are specific embodiments of the retraction device of the present invention in the folded and the DEPLOYED CONFIGURATIONs.
Figure 4B:
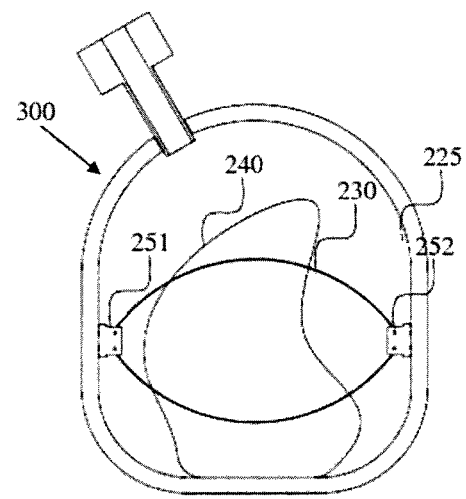

Reference is now made to FIGS. 4a-b, which illustrate a specific embodiment of the retraction device of the present invention.

This figure illustrates a—canula 218 which has been generated by the operator (e.g., surgeon) in abdominal cavity 220 for performing a minimally invasive surgery or a laparoscopic surgery. As part of the surgery, there might be a need to retract organ 240. This may be performed via the retraction device 300 of the present invention. According to this embodiment, retraction device 300 comprises a supporting member 230 which interconnects between a first and a second anchoring means 251 and 252. According to this figure, first and a second anchoring means 251 and 252 are connectable to the abdominal wall 225.

According to these figures, retraction device 300 has at least two configurations a FOLDED CONFIGURATION (see FIG. 4a) and a DEPLOYED CONFIGURATION (see FIG. 4b).

FIG. 4a illustrates the retraction device 300 in its FOLDED CONFIGURATION, in which the retraction device 300 is shaped and sized so as to be inserted into abdominal cavity 220 though a canula 218.

FIG. 4b illustrates the retraction device 300 in its DEPLOYED CONFIGURATION in which the retraction device 300 is deployed within the abdominal cavity and can be connected to abdominal wall 225. In the DEPLOYED CONFIGURATION, the retraction device 300 can be used to retract organ 240.

It should also be emphasized that according to different embodiments of the present invention, the default configuration of the retraction device may be the FOLDED CONFIGURATION, or the DEPLOYED CONFIGURATION. The term 'default configuration' refers hereinafter to the size and shape of the retraction device when the same is not constrained within the insertion canula 218.

According to some embodiments, the FOLDED and the DEPLOYED CONFIGURATIONs of retraction device 300 may be provided by folding and deploying supporting member 230.

In this embodiment, supporting member 230 is constructed of at least two leaf springs which may be bent by the operator (e.g., physician, surgeon, etc.) by approximation of first and second anchoring means 251 and 252 for the deployment of retraction device 300.

According to different embodiments of the present invention, a tangential force which is applied on the device of the present invention, is a force which is applied on the tangential direction for folding or deploying the device of the present invention by changing the shape of the same. The tangential force differs from any other force in another direction. For example, the tangential force is different from a retraction force which does not change the shape (e.g., bents) of the supporting member of the present invention.

In other words, in this embodiment, in the FOLDED CONFIGURATION, the two leaf springs are in their relaxed configuration (default configuration) and in the DEPLOYED CONFIGURATION the two leaf springs are in their deformed (loaded) configuration (i.e., bent).

In the DEPLOYED CONFIGURATION, the first and second anchoring means 251 and 252 are pushed towards the direction of abdominal wall 225, such that retraction device 300 is held within the abdominal cavity in said DEPLOYED CONFIGURATION. Namely, when device is released in retraction position the loaded springs push the anchoring means toward the abdominal wall.

However, as mentioned above, it should be pointed out that according to some embodiments, in the FOLDED CONFIGURATION, the two leaf springs are in their deformed configuration (i.e., bent), and in the DEPLOYED CONFIGURATION the two leaf springs are in their relaxed configuration.

According to this embodiment, the retraction device may be provided to the abdominal cavity when the leaf springs are bent (or folded in a manner know in the art), and the deployment of the retraction device may be performed by straightening the leaf springs.

According to a specific embodiment, the leaf springs composing the supporting member 230 are at least partially connected to a first and a second anchoring means.

It should be mentioned that in spite of the ability of the leaf springs to be bent by an operator for their deployment, the same are substantially not deformed when mechanical force of an organ (i.e., perpendicular forces) is actuated on the retraction device.

The retraction device 300 which is illustrated in FIG. 4a is introduced in its FOLDED CONFIGURATION through canula 218 (which has a diameter of 5-15 mm) into internal abdominal cavity 220.

The retraction device 300 which is illustrated in FIG. 4b is provided in the DEPLOYED CONFIGURATION.

The reconfiguration of retraction device 300 from the FOLDED CONFIGURATION to the DEPLOYED CONFIGURATION is performed by approximating the first and second anchoring means 251 and 252 relatively to each other while positioning the retraction device 300 in a predetermined position (i.e., angle) and in a predetermined location.

Now the organ is place on the supporting member of the retraction device. Next, the first and the second anchoring means 251 and 252 are released. As a result of that, organ 240 which actuates a predetermined force on the retraction device 300, is retracted.

According to this embodiment, retraction device 300 in the DEPLOYED CONFIGURATION forms a surface which is characterized a 2D geometrical structure. According to this embodiment, the first and the second anchoring means 251 and 252 are connected to the abdominal wall due to pressure of the abdominal wall on retraction device 300 and vice versa. As a result of the pressure, retraction device 300 is held in its predetermined location, and is not movable due to friction forces between the recreation device and the abdominal wall.

For summary, it should be mentioned that retraction device 300 is characterized by an ability to resist to perpendicular force actuated on the same by a retracted organ, and on the other side they don't resist a tangential forces which are adapted to deploy the device.

According to various embodiments of the present invention, the supporting member of the retraction device may also be characterized by an additional configuration in which the device is in between the folded and DEPLOYED CONFIGURATION.

Reference is now made to FIGS. 5a-5b, which illustrates another embodiment of the present invention.

According to this figure, retraction device 400 is constructed of a first anchoring means 310 and a second anchoring means 320, which are interconnected via supporting member 330. Supporting member 330 comprises of three rods 331, 332 and 333 which are connected each other by hinges 326, 327. In this embodiment, supporting member 330 is a foldable member characterized by at least two configurations: a FOLDED CONFIGURATION (see FIG. 5a); and, a DEPLOYED CONFIGURATION (illustrated in FIG. 5b).

The supporting member 330 is connected to anchoring means 310 and 320 by hinges 328 and 325. The deployment of supporting member 330 may be performed by rotating the hinged members of supporting member 330 relatively to each other, and thereby forming a 2D geometrical structure. For example, according to the embodiment of FIGS. 5a-5b, rods 331 and 333 can be rotated with respect to rod 332 in hinges 326 and 327.

In the embodiment illustrated in FIGS. 5a-5b, rods 331 and 333 are connected to a tension spring (not shown) which is located within hollow rod 332. Rods 331 and 333 may be either (a) rotated by the operator (for the reconfiguration into the FOLDED CONFIGURATION); or, (b) rotated by a spring (which aspires to be in the DEPLOYED CONFIGURATION, as in FIG. 5b). In the second option, the tension spring is adapted to actuate a pulling force on rods 331 and 333, to return to its initial position (default configuration)—the DEPLOYED CONFIGURATION illustrated in FIG. 5b. In the FOLDED CONFIGURATION (see FIG. 5a), when rods 331, 332 and 333 are substantially align to each other, and the tension spring is tensed, retraction device 400 may be introduced into the abdominal cavity through a canula, and then deployed within the abdominal cavity (by letting the tension spring to return rods 331 and 333 to their initial position). The straightening of the supporting member (to provide the FOLDED CONFIGURATION) may be performed to pulling first and second anchoring means 310 and 320 to the opposite directions.

It should be mentioned that although the ability of retraction device 400 to be lengthened in its main axis, it is not deformable in the axis of the force which is actuated by a retracted organ.

According to the embodiment of the present invention, which is illustrated in FIGS. 5a-5b, the first anchoring means 310 and a second anchoring means 320 of retraction device 400 are clamps which are adapted to grasp the abdominal wall at the anchoring points.

According to one embodiment of the present invention, the actuation of the anchoring means (310 and 320) is provided by a 2 shoulders (rings) mechanism 340. The 2 rings mechanism 340 comprises 2 rings 341 and 342.

When the two rings are brought into proximity to one another, the anchoring means are actuated. Thus, as can be seen in FIG. 5b, the two left shoulders (rings) are brought into proximity to one another; thus, the anchoring means 310 are actuated. On the contrary, the two right shoulders (rings) are not brought into proximity to one another; thus, the anchoring means 320 are not actuated.

It should also be mentioned that according to different embodiments of the present invention, the default configuration of the retraction device may be the FOLDED CONFIGURATION, the DEPLOYED CONFIGURATION, or any other position between the FOLDED CONFIGURATION and the DEPLOYED CONFIGURATION.

It should be emphasized that the above disclosed device is constructed from a plurality of rigid rods ('arms') hinged-like coupled to one another. Such a construction is aimed to:
  (a) enable all the rods to be straightened into a single 1D 'line' so as to be introduced into the abdominal cavity through a canula (diameter of 5-15 mm) whilst minimum application of force.
  (b) Enabling displacement and approximation of first and second anchoring means according to the desired anchoring point (which vary in the different anatomical cavities), whilst minimum application of force.

All of the above is enabled while the device is not substantially deformed out side the plane defining the supporting member. It should be pointed that the device may be deformed in the plane defining the supporting member.

Figure 6:
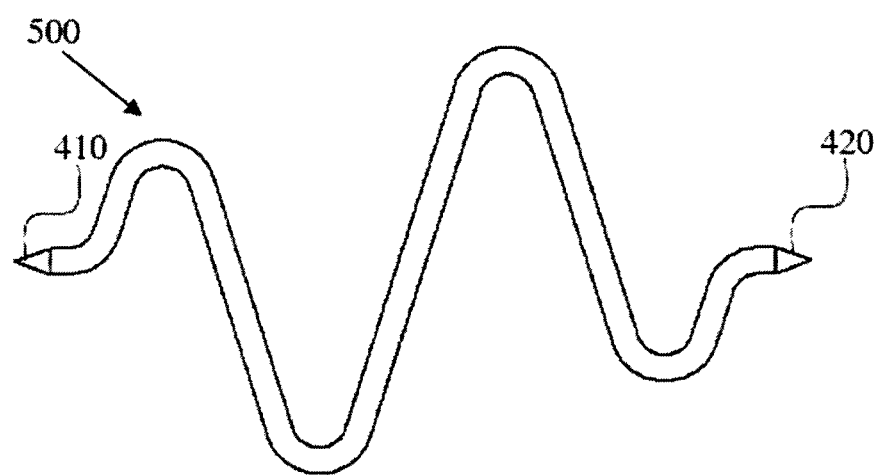
FIG. 6 is a specific embodiment of the retraction device of the present invention in its DEPLOYED CONFIGURATION.

Reference is now made to FIG. 6, which illustrates another embodiment of the present invention. According to this figure, retraction device 500 is rod with a snake-like shape (a spring-like device), which may be folded and deployed according to the various needs. For example, for the introduction of retraction device 500 into the abdominal wall, the same may be in a straight (1D) configuration (FOLDED CONFIGURATION) when released inside the body cavity it becomes back to default configuration. The snake-like shape of retraction device 500 is adapted to form a surface which is adapted to support the retracted organ.

According to a specific embodiment, following the introduction to the abdominal wall, retraction device 500 may be constricted, and thereby reconfigured into the DEPLOYED CONFIGURATION. This may be performed manually by the operator, or automatically as mentioned above. In this case, the default configuration may be a configuration which is between the FOLDED CONFIGURATION and the DEPLOYED CONFIGURATION. The retraction device 500 of FIG. 6 has first and second anchoring means 410 and 420 which are characterized by sharpened ends (e.g., pegs). The reconfiguration of retraction device 500 from the default configuration to the DEPLOYED CONFIGURATION may be performed by approximating first and second anchoring means 410 and 420. Following the positioning of pressed retraction device 500 within the abdominal cavity, these first and second anchoring means 410 and 420 are adapted to be anchored (e.g., stuck) within the abdominal wall when the retraction device 500 is automatically converted to the DEPLOYED CONFIGURATION willing to be in the default configuration.

According to various needs of the operator, retraction device 500 may also be lengthened to a predetermined length to be in the FOLDED CONFIGURATION (like tensioning a spring).

The force which is needed for the reconfiguration of the retraction device in its various embodiments from the FOLDED CONFIGURATION to the DEPLOYED CONFIGURATION, and vice versa, is a standard force which operators are used to apply via graspers.

It should be emphasized that it is within the scope of the present invention in which the default configuration of the retraction device 500 is the DEPLOYED CONFIGURATION and by applying forces on the same, its converted into is FOLDED CONFIGURATION. Alternatively it is within the scope of the present invention in which the default configuration of the retraction device 500 is the FOLDED CONFIGURATION and by applying forces on the same, it is converted into is DEPLOYED CONFIGURATION.

Reference is now made to FIGS. 7a1-7a3, which illustrate another embodiment of the present invention. According to this figure, retraction device 600 is a telescopic device which may be deployed by its elongation within the abdominal wall.

Retraction device 600 comprises supporting member 530 which is adapted to form a supporting surface, when side rods 535 are deployed (in the DEPLOYED CONFIGURATION). Supporting member 530 comprises an internal telescopic rod 531 and external telescopic rod 532 (see FIGS. 7a2-7a3).

The external telescopic rod 532 comprises a spring which pushes internal telescopic rod 531, so that the default configuration of retraction device 600 is when internal telescopic rod 531 is extending out of external telescopic rod 532 (i.e., the DEPLOYED CONFIGURATION).

Internal telescopic rod 531 comprises a first anchoring means 537 at one of its ends, and external telescopic rod 532 comprises a second anchoring means 538 at one of its ends.

Side rods 535 are connected to supporting member 530 via torsion springs. Side rods 535 are adapted to extend out of external telescopic rod 532 in a substantially perpendicular angle relatively to the same.

The torsion springs are adapted to push side rods 535, so that in the default configuration, side rods 535 are deployed.

According to this embodiment, the default configuration of retraction device 600 is the DEPLOYED CONFIGURATION.

Retraction device 600 is introduced through a canula into the abdominal cavity in its FOLDED CONFIGURATION. In this configuration, side rods 535 are folded within external telescopic rod 535.

Following the introduction of retraction device 600 to the abdominal cavity, it is reconfigured to the DEPLOYED CONFIGURATION in a predetermined location and a predetermined position (i.e., angle).

In this position, first and second anchoring means (e.g., pegs) are stuck within the abdominal wall, while internal telescopic rod 531 is at least partially within the external telescopic rod 532; and the spring within external telescopic rod 532 pushes out the internal telescopic rod 531, so that retraction device 600 is fixed in said predetermined position and location.

It is within the scope of the present invention to use either a dedicated grasping means or a standard grasping means (540) to enable the attachment of the anchoring means 538 and 537 to the abdominal wall.

Furthermore, in the DEPLOYED CONFIGURATION, side rods 535 are extending out of external telescopic rod 532, creating a supporting surface to retract an organ.

According to some embodiments, retraction device 600 may be used for retraction of an organ when side rods 535 which are maintained within external rod 532 and are not extracted from the same. In this embodiment, retraction device 600 is a 1D telescopic rod which can be used for retraction of an organ (see further details in FIGS. 7B-7D).

In case of a plurality of 1D telescopic rods which are used for a retraction of an organ (placed one next to the other), a 2D supporting surface is created, and an organ may also be retracted. In this embodiment the plurality of 1D telescopic rods can be coupled/interconnected to each other or may be used separately/independently.

Figure 7B:
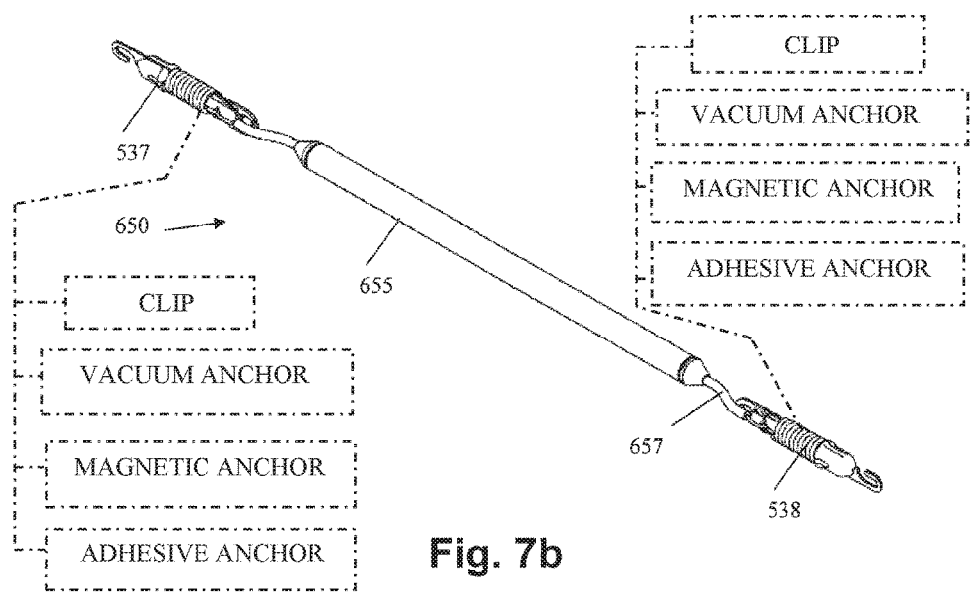
FIG. 7b-7d are specific embodiments of a telescopic retraction device of the present invention in its FOLDED and DEPLOYED CONFIGURATIONs.
Figure 7C:
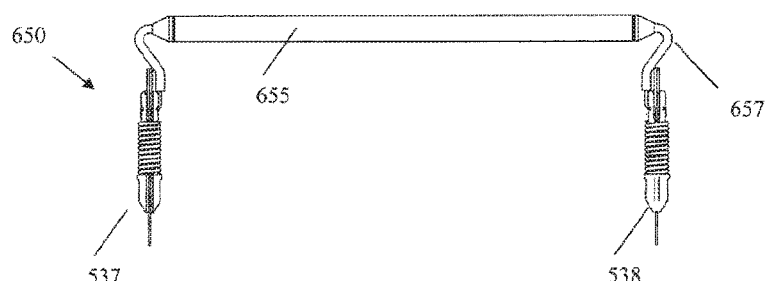
Figure 7D:
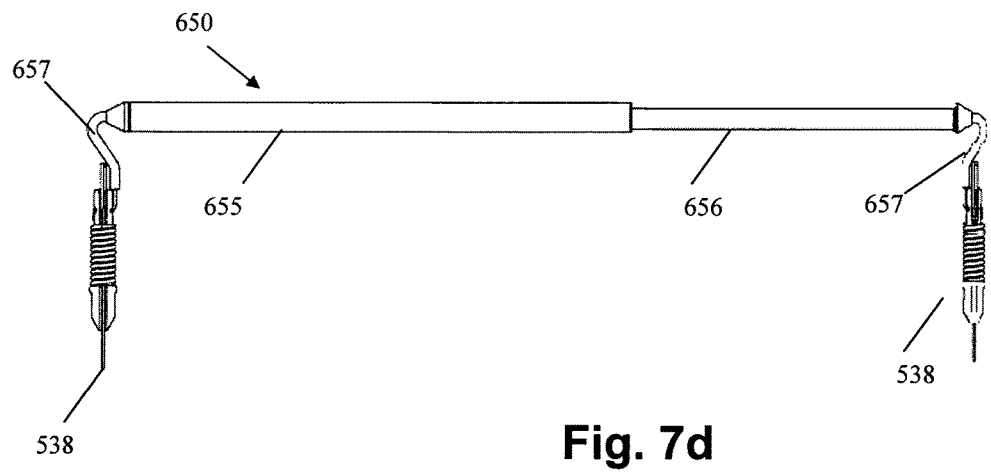

Reference is now made to FIGS. 7b-7d, which illustrate another embodiment of the present invention. According to this figure, retraction device 650 is a telescopic device which may be deployed by its elongation within the abdominal wall.

Retraction device 650 is essentially the same as retraction device 600; However, the same illustrates an embodiment without the side rods 535.

As mentioned above, according to some embodiments of the present invention, the retraction device 650 may be characterized by a 1D, a 2D or a 3D geometrical structure.

According to various embodiments, the retraction device 650 may take the form of at least one of the following structures: a plurality of rods-like retraction device 650 (in parallel), an array of interconnected rods-like (or wires-like) retraction device 650.

While FIG. 7b illustrates the telescopic retraction device 650 in the close (FOLDED) CONFIGURATION (in said configuration, the telescopic retraction device is introduced through a canula into the abdominal cavity); FIGS. 7c&7d illustrate the telescopic retraction device 650 in the DEPLOYED CONFIGURATION (and default configuration, once the same have been already introduced into the abdominal wall) where both the external and the internal rods (655 and 656 respectfully) are shown (see FIG. 7d).

It should be pointed out that according to this embodiment, in the FOLDED CONFIGURATION (FIG. 7b), the device is introduced into the abdominal cavity via a canula, thus, the anchoring means 538 and 537 are parallel to the main longitudinal axis of the device. In the DEPLOYED CONFIGURATION (see FIGS. 7c-7d) the anchoring means 538 and 537 are can be oriented at any angel relatively to the main longitudinal axis of the device.

While both FIGS. 7c and 7d illustrates the telescopic retraction device 650 in the DEPLOYED CONFIGURATION, 7d illustrates the same while its stretch, and thus, the internal rod 656 is at least partially outside the external rod 655.

It should be pointed that although the telescopic retraction device 650 may be extended and stretched (due to the telescopic properties of the same); however such stretching is not essential necessity.

Thus, it may very well be that the DEPLOYED CONFIGURATION and the FOLDED CONFIGURATION of telescopic retraction device 650 are of the same length.

Also shown are coupling means 657 coupling the anchoring means 538 to the telescopic retraction device 650 at both its ends. According to one embodiment, the coupling means 657 enables the rotation of the anchoring means 538 and 537 around the main longitudinal axis of the rods (655 and 656).

Yet more, according to one embodiment, the coupling means 657 reconfiguration of the anchoring means 538 and 537 from being parallel to said main longitudinal axis (when the telescopic retraction device 650 is introduced through the canula, i.e., in the FOLDED CONFIGURATION) to being positioned substantially perpendicularly to the same.

According to another embodiment the coupling means 657 enables the anchoring means 538 and 537 to be orientated at an angle A with respect to the same. Said angle A can be in a range of degrees to 90 degrees.

The anchoring means 538 in FIGS. 7*b*-7*c* are clips. However, said anchoring means can be selected from the group consisting of: vacuum means, magnetic means; mechanical means, adhesive means or any combination thereof.

According to some embodiments of the present invention, the telescopic retraction device 650 may comprises the 2 shoulders (rings) mechanism 340 (so as to actuate the anchoring means) disclosed in FIG. 5.

Figure 8:
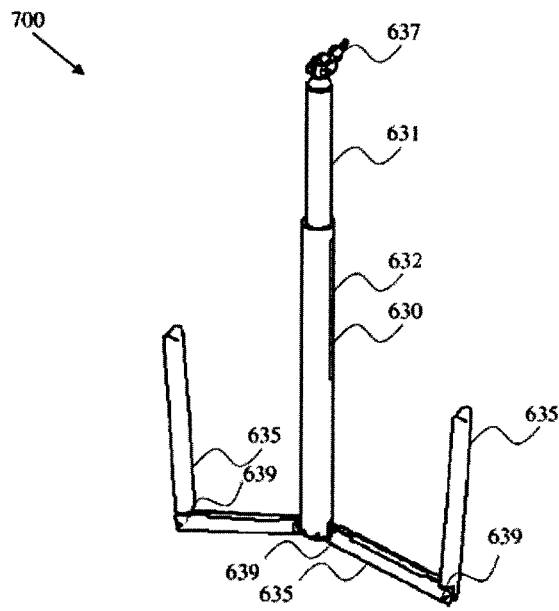
FIG. 8 is a specific embodiment of a telescopic retraction device of the present invention in its DEPLOYED CONFIGURATION.

Reference is now made to FIG. 8, which illustrates another embodiment of the present invention.

According to this figure, retraction device 700 is telescopic device which may be deployed by its elongation within the abdominal wall.

Retraction device 700 comprises supporting member 630 which is adapted to form a supporting surface, when side rods 635 are deployed. Retraction device 700 may comprise spring elements adapted to fix the same in its DEPLOYED CONFIGURATION.

Retraction device 700 comprises supporting member 630 which is adapted to form a supporting surface, when side rods 635 are deployed (in the DEPLOYED CONFIGURATION). Supporting member 630 comprises an internal telescopic rod 631 and external telescopic rod 632. External telescopic rod 632 comprises a spring which pushes internal telescopic rod 631, so that the default configuration of retraction device 700 is when internal telescopic rod 631 is out of external telescopic rod 632 (the DEPLOYED CONFIGURATION). Internal telescopic rod 631 comprises a first anchoring means 637 at one of its ends, and external telescopic rod 632 comprises a second anchoring means which are parts of side rods 635.

According to a specific embodiment of retraction device 700, rods 635 are adapted to create a surface which leans on different organs (e.g., intestine), thereby scatter to load of the device of the internal abdominal wall.

According to a specific embodiment, side rods 635 are connected to supporting member 630 via hinges 639, and are supported with springs. Side rods 635 are extending out of one end of external telescopic rod 632. According to a specific embodiment, the springs which are connected to side rods 635 are adapted to pull side rods 635, so that in the default configuration (the DEPLOYED CONFIGURATION) is formed.

According to other embodiments, side rods 635 may be provided without springs, and their deployment is performed by rotating them manually so that a predetermined supporting surface is formed.

Retraction device 700 is introduced through a canula into the abdominal cavity in its FOLDED CONFIGURATION. In this configuration, side rods 635 are folded to the sides of external telescopic rod 635. The introduction of retraction device 700 to the abdominal cavity is aided via introducer (not shown).

Following the introduction of retraction device 700 to the abdominal cavity in the FOLDED CONFIGURATION, it is reconfigured to the DEPLOYED CONFIGURATION. Said reconfiguration is performed in a predetermined location (within the abdominal cavity) and at predetermined position (i.e., angle).

In this position, first and second anchoring means (e.g., pegs) 637 are stuck (i.e., anchored) within the abdominal wall, while internal telescopic rod 631 is at least partially out of said external telescopic rod 632, and the spring within external telescopic rod 632 pushes internal telescopic rod 631, so that retraction device 700 is fixed in said predetermined position and location.

Furthermore, in the DEPLOYED CONFIGURATION, side rods 635 are extending out of external telescopic rod 632, creating a supporting surface to retract an organ.

According to this embodiment, retraction device 700 may be operated via a shifting device with a loop in its end.

According to some embodiments, retraction device 700 may be used for retraction of an organ when side rods 635 are located at the side external rod 532, perpendicular to the same (at this position, side rods 535 are not deployed). In this embodiment, retraction device 700 is a 1D telescopic rod. When two 1D telescopic rods are used, an organ may also be retracted.

Figure 9:
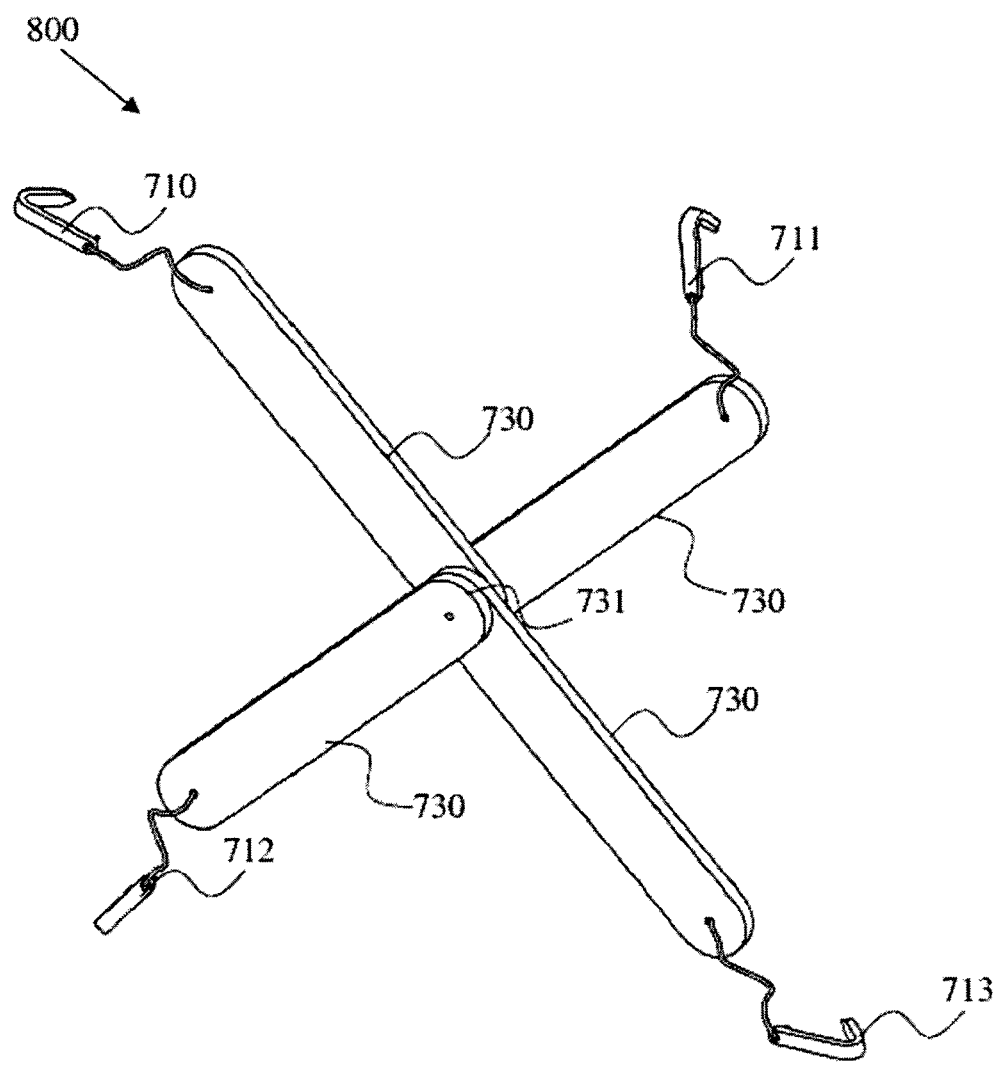
FIG. 9 is a specific embodiment of X-type retraction device of the present invention in its DEPLOYED CONFIGURATION.

Reference is now made to FIG. 9, which illustrates another embodiment of the present invention.

According to this figure, retraction device 800 has four anchoring elements 710, 711, 712 and 713, which are connectable to the abdominal wall. Retraction device 800 has form of X-shape device in its DEPLOYED CONFIGURATION, and an elongated from in the FOLDED CONFIGURATION.

According to other embodiment, the retraction device may have n anchoring elements, which are connectable to the abdominal wall, wherein n is a natural number and n≥2.

The deployment of retraction device 800 may be performed by rotation of elements 730 relatively to each other around axis 731, so as to form said X-shape.

In the DEPLOYED CONFIGURATION, retraction device 800 has an X-shaped supporting surface which is adapted to support a retracted organ.

It should be emphasized that it is within the scope of the present invention in which according to one embodiment at least two, preferably 3 anchoring elements are provided.

According to another embodiment of the present invention there could be provided any intermediate member connecting said supporting member and the anchoring means.

Reference is now made to FIGS. 10-14 in which illustrated the use of the retraction device.

Figure 10A:
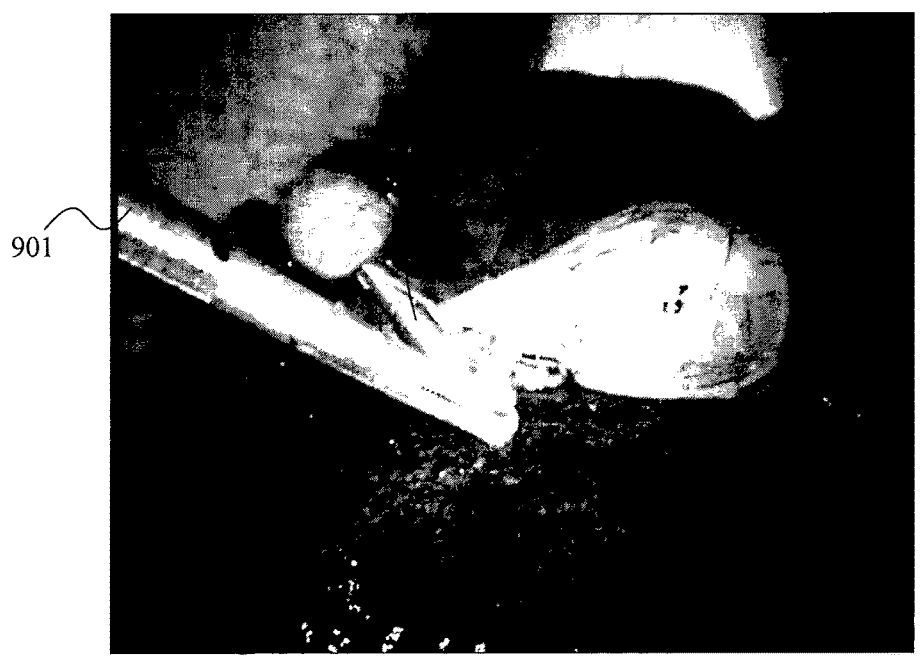
FIGS. 10a, 11a, 12a, 13a and 14a are illustrations of the retraction device of the present invention in experimental settings.
Figure 10B:
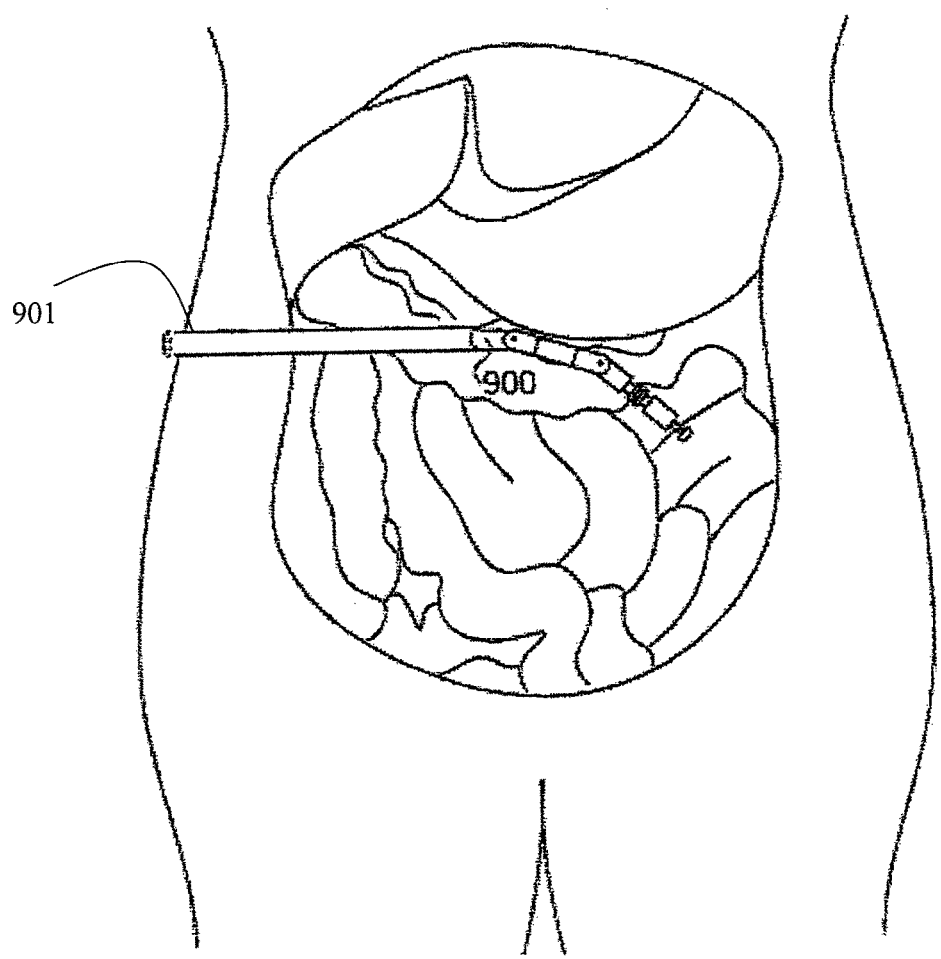

FIG. 10*a* illustrates the retraction device 900 (which is similar to the embodiment of retraction device 400) when it is introduced into the abdominal cavity through a canula 901. FIG. 10*b* is a schematic illustration of the same.

Figure 11A:

In FIG. 11*a*, retraction device 900 is being positioned; i.e., brought in proximity to liver 850.

Figure 11B:
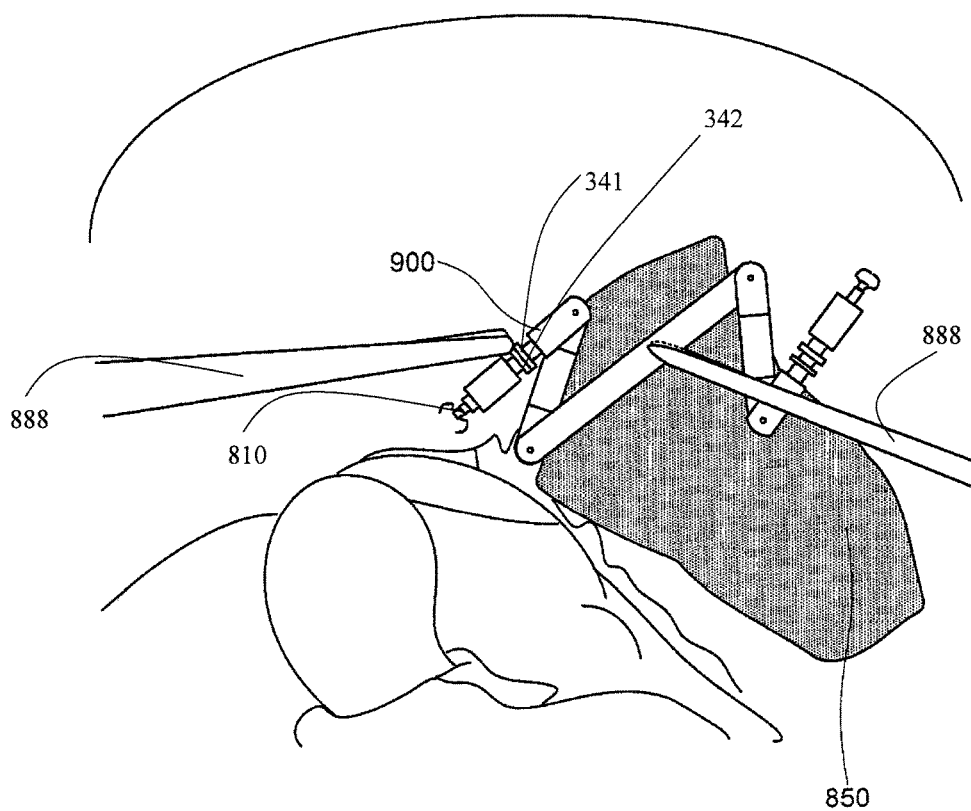

FIG. 11*b* is a schematic illustration of the same.

FIG. 11*b* also illustrates the activation/actuation of the anchoring means 810 by closely bringing rings 341 and 342 (be means of a grasper).

Figure 12A:

In FIG. 12*a*, a first anchoring means 810 of retraction device 900 (in the DEPLOYED CONFIGURATION) is connected/anchored to the abdominal wall.

Figure 12B:
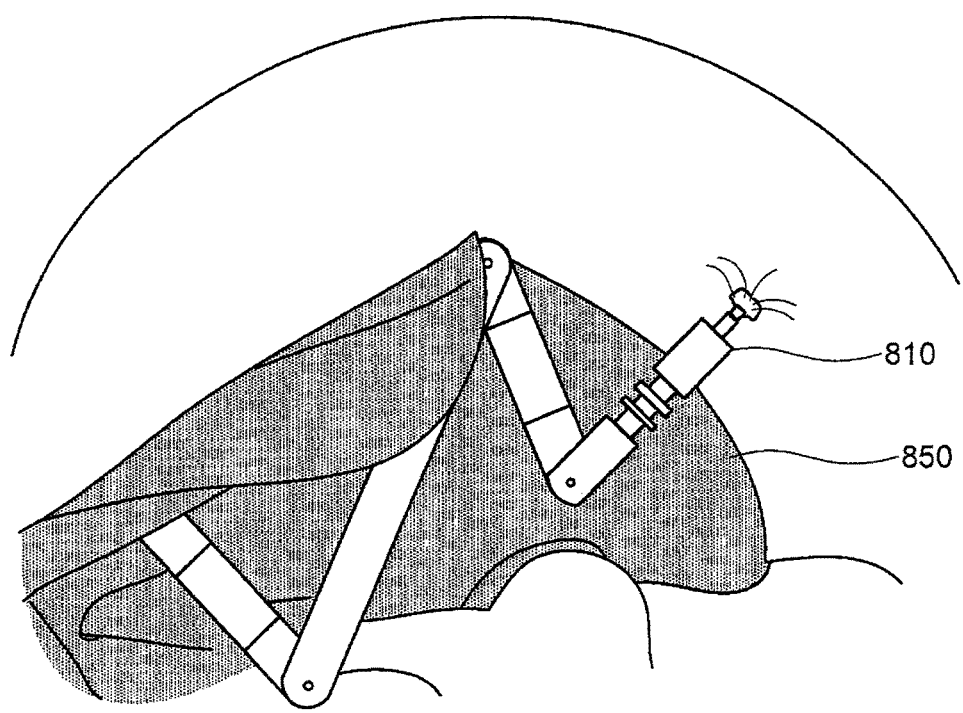

FIG. 12b is a schematic illustration of the same.

Figure 13A:
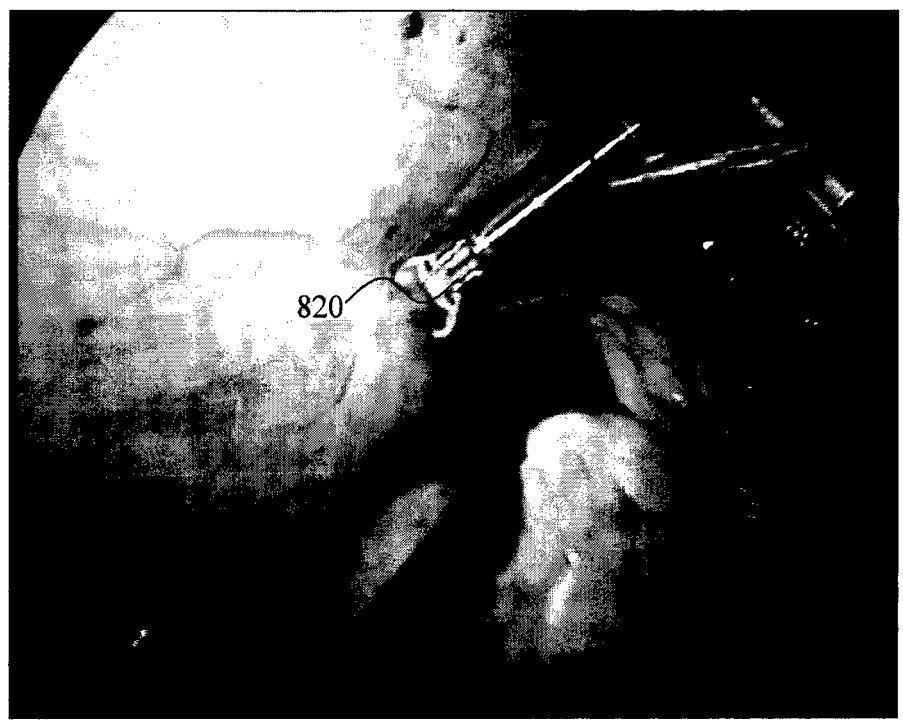

In FIG. 13a, the second anchoring means 820 of retraction device 900 is connected to the abdominal wall.

Figure 13B:
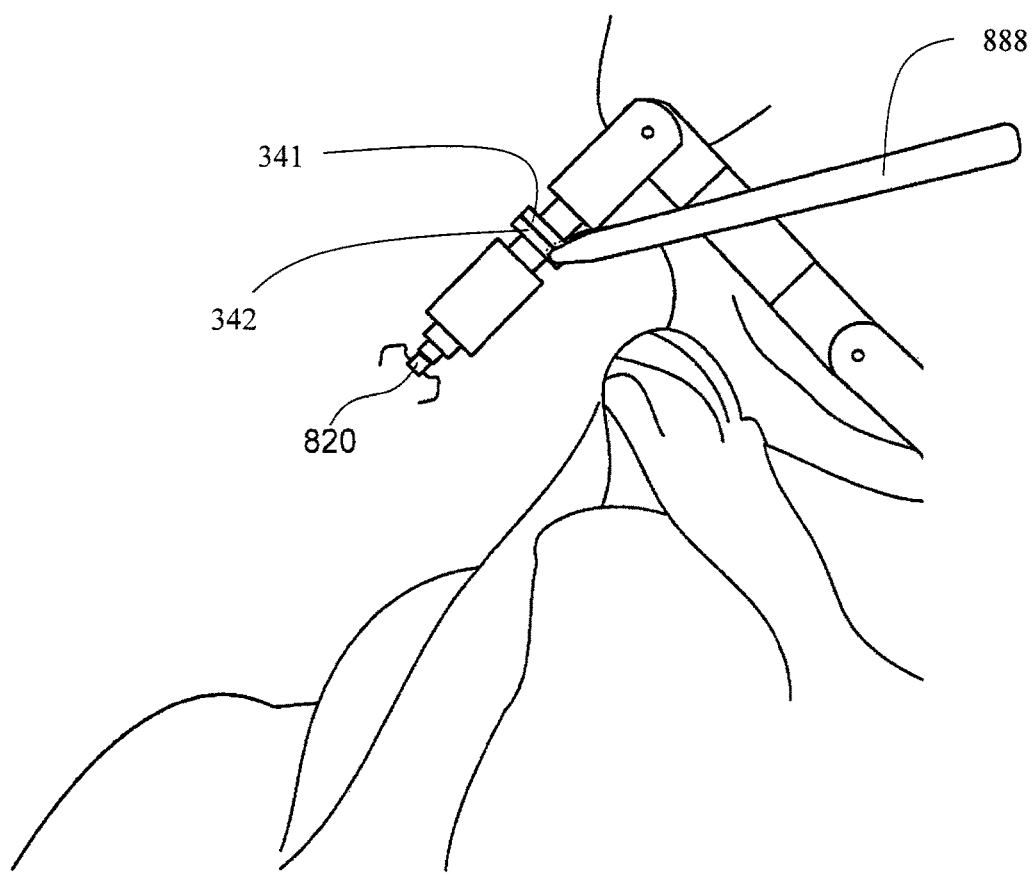

FIG. 13b also illustrates the activation/actuation of the anchoring means 820 by closely bringing rings 341 and 342 (be means of grasper 888).

FIG. 13b is a schematic illustration of the same.

Figure 14A:
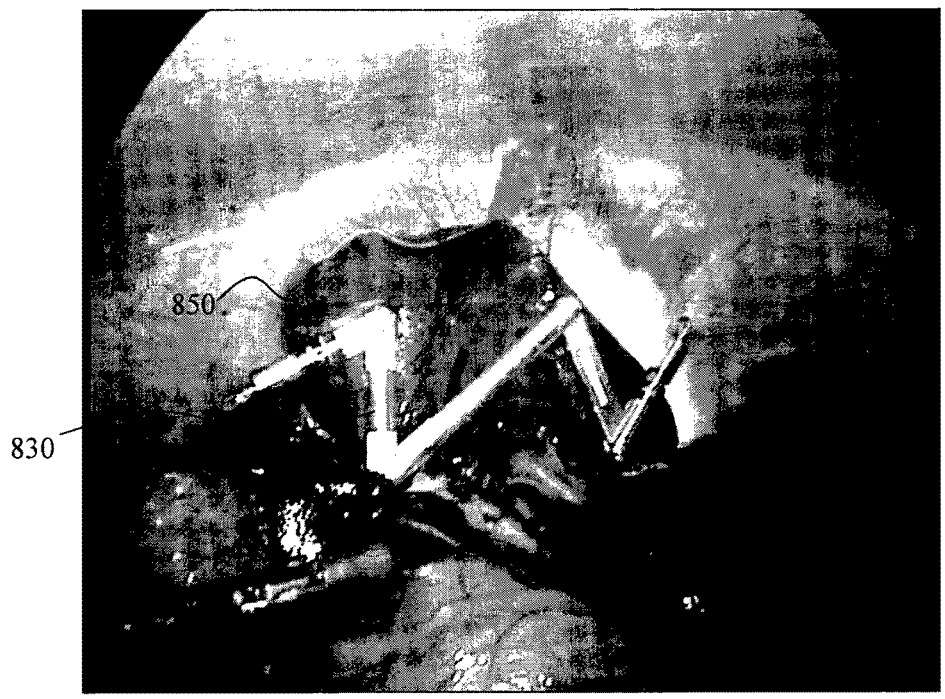

FIG. 14a illustrates the final result of the above mentioned retraction process. In this figure, the supporting member 830 of retraction device 900 supports liver 850. As can be seen, the retraction device 900 is substantially not deformed when mechanical force is applied on the same by liver 850. In other words, retraction device 900, and more specifically the surface formed by supporting member 830 is not bent/curved/twisted, etc.

Figure 14B:
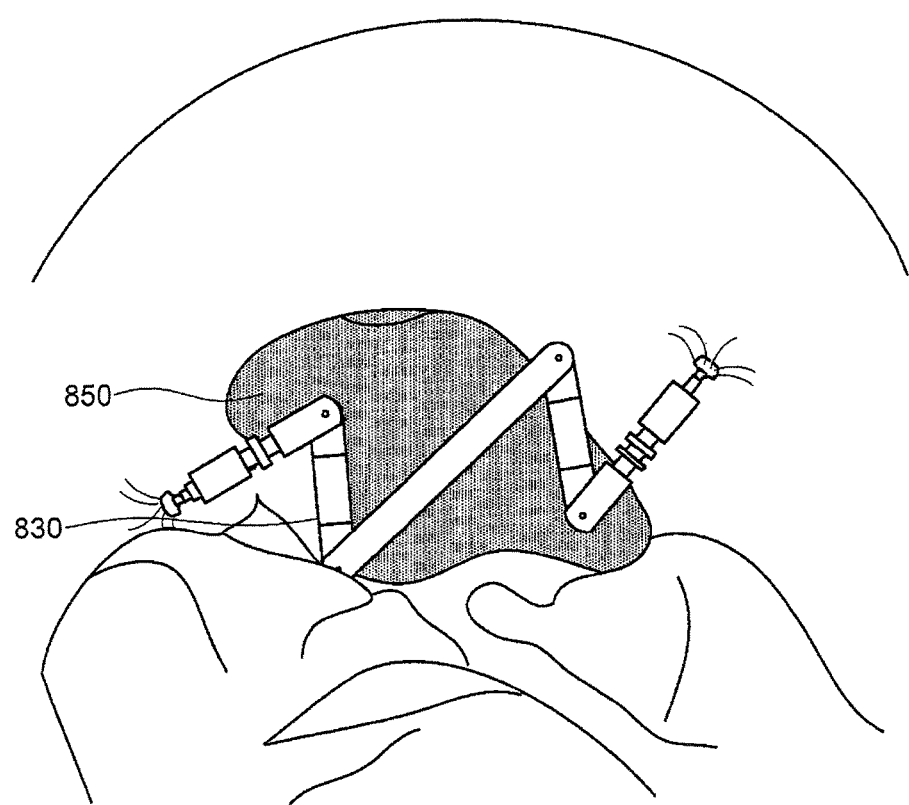

FIG. 14b is a schematic illustration of the same.

To summarize the above, the supporting member is characterized by the following:

a. The supporting member may be conducted/provided into the abdominal cavity through a canula with diameter of 5-15 mm, and deployed with said cavity.

b. The supporting member is not deformable when a perpendicular mechanical force of the retracted organ (due to its weight which may be max. a few kg.) is applied on it.

c. The supporting member may have more than two configurations (e.g., a configuration between the FOLDED CONFIGURATION and the DEPLOYED CONFIGURATION).

d. The supporting member may comprise internal reinforcing elements adapted to prevent the same to be converted from said DEPLOYED CONFIGURATION to said FOLDED CONFIGURATION.

e. The supporting element may comprise: a telescopic element with a plurality of arms, a foldable rod with hinged elements, a plurality of hinged elements.

According to different embodiments, the first and the second anchoring means may be characterized by an ability to penetrate and not the penetrate the abdominal wall.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A retraction device comprising:
an internal telescopic rod comprising a first anchor attached to one end thereof by a first coupler; and
an external telescopic rod comprising a second anchor attached to one end thereof by a second coupler, said internal telescopic rod arranged for sliding longitudinally in said external telescopic rod and said internal telescopic rod is concentric with an inner diameter of said external telescopic rod, and wherein each of said first coupler and said second coupler enables rotation of said first anchor and said second anchor around main longitudinal axes of said internal telescopic rod and said external telescopic rod, respectively;
and wherein said first anchor and said second anchor are actuated by rings that are parallel to each other, wherein planar faces of said rings are selectively brought towards each other or away from each other.

2. The retraction device according to claim 1, wherein each of said first coupler and said second coupler is movable between positions collinear and not collinear with respect to said main longitudinal axes of said internal telescopic rod and said external telescopic rod, respectively.

3. The retraction device according to claim 2, wherein in said collinear positions of said first coupler and said second coupler, said first anchor and said second anchor are not collinear but are parallel with respect to said main longitudinal axes of said internal telescopic rod and said external telescopic rod, respectively.

4. The retraction device according to claim 1, wherein when said first coupler and said second coupler are not collinear with respect to said main longitudinal axes of said internal telescopic rod and said external telescopic rod, respectively, said first coupler and said second coupler are perpendicular to said main longitudinal axes of said internal telescopic rod and said external telescopic rod, respectively.

5. The retraction device according to claim 1, wherein for each of said first anchor and said second anchor, movement of said rings into proximity to one another actuates said anchor.

6. The retraction device according to claim 1, wherein said first anchor and said second anchor comprise anchor hooks or vacuum anchors.

7. The retraction device according to claim 1, wherein said first anchor and said second anchor comprise anchor hooks or magnetic anchors.

8. The retraction device according to claim 1, wherein said first anchor and said second anchor comprise anchor hooks or mechanical clips.

9. The retraction device according to claim 1, wherein said first anchor and said second anchor comprise anchor hooks or adhesive anchors.

* * * * *